US005710104A

United States Patent [19]

Magin et al.

[11] Patent Number: 5,710,104
[45] Date of Patent: Jan. 20, 1998

[54] GLYPHOSATE COMPOSITIONS COMPRISING POLYETHOXYLATED MONOHYDRIC PRIMARY ALCOHOLS

[75] Inventors: Ralph W. Magin; Joe D. Sauer; John R. Maloney, all of Baton Rouge, La.

[73] Assignee: Albemarle Corporation, Richmond, Va.

[21] Appl. No.: 628,567

[22] Filed: Apr. 3, 1996

[51] Int. Cl.$^6$ .......................... A01N 25/30; A01N 57/02
[52] U.S. Cl. .......................................................... 504/206
[58] Field of Search ............................................. 504/206

[56] References Cited

U.S. PATENT DOCUMENTS

| | | | |
|---|---|---|---|
| 3,887,624 | 6/1975 | Gipson et al. | 260/615 B |
| 3,952,068 | 4/1976 | Gipson et al. | 260/632 R |
| 4,400,196 | 8/1983 | Albrecht et al. | 71/86 |
| 4,931,080 | 6/1990 | Chan et al. | 71/87 |
| 5,047,079 | 9/1991 | Djafar et al. | 71/86 |

FOREIGN PATENT DOCUMENTS

| | | |
|---|---|---|
| 0617894 | 10/1994 | European Pat. Off. . |
| 9516351 | 6/1995 | WIPO . |
| 9600010 | 1/1996 | WIPO . |

OTHER PUBLICATIONS

Wyrill, III, J. B. and Burnside, O. C.—"Glyphosate Toxicity to Common Milkweed and Hemp Dogbane as Influenced by Surfactants", Weed Science, vol. 25 Issue 3 (May), 1977, pp. 275–287.

Primary Examiner—S. Mark Clardy
Attorney, Agent, or Firm—Philip M. Pippenger

[57] ABSTRACT

Glyphosate formulations which are effective even when employed at dosages below the dosage currently recommended for post-emergent herbicidal or plant growth regulant use are described. They are formulated as water solutions or powders or granules of (a) one or more agriculturally acceptable amine, alkali metal, alkylsulfonium, alkylphosphonium, sulfonylamine, and/or aminoguanidine salts of glyphosate; and (b) one or more water-soluble polyethoxylated monohydric primary alcohol having a β-branched alkyl group which has a total of at least about 10 carbon atoms and at least about 3 carbon atoms in the branch on the β-carbon atom or agriculturally acceptable salt or ester thereof.

33 Claims, No Drawings

GLYPHOSATE COMPOSITIONS COMPRISING POLYETHOXYLATED MONOHYDRIC PRIMARY ALCOHOLS

TECHNICAL FIELD

This invention relates to glyphosate formulations which are effective even when employed at dosages below the dosage currently recommended for post-emergent herbicidal use against undesired vegetation.

BACKGROUND

Glyphosate, N-(phosphonomethyl)glycine, is a well-known widely used herbicide. It is generally employed in the form of an agriculturally acceptable salt.

In U.S. Pat. No. 5,116,401 to D. C. Young it is pointed out that although glyphosate is a very active, broad spectrum, systemic, relatively environmentally safe herbicide, its solubility in water at 25° C. is only 1.2 weight percent and many of its homologs and salts are only slightly soluble or are essentially insoluble in water and organic solvents. Thus in practice, formulations of glyphosate salts with other components to enhance its solubility and its effectiveness are typically used.

Over the years a wide variety of substances, including surfactants, have been studied or proposed as adjuvants to enhance the effectiveness of glyphosate. For example, J. W. Kassebaum and H. C. Berk indicate in U.S. Pat. No. 5,317,003, that surfactants are usually employed to enhance the effectiveness of glyphosate when it is applied to the foliage of various plants, and that the most widely used surfactant in commercial compositions is an ethoxylated fatty amine. In addition, they refer to knowledge in the art that a particular surfactant used in an aqueous composition with a herbicide can enhance the effectiveness of the herbicide, whereas other surfactants have very little, if any, beneficial effect. They also note that some surfactants may exhibit antagonistic effects. As an example they cite the work of Wyrill and Burnside, *Weed Science*, Volume 25, (1977), pages 275–287 wherein, among other things, it was found that the surfactant ETHOQUAD 18/12 was relatively ineffective in enhancing phytotoxicity of glyphosate to hemp dogbane whereas in a separate experiment an analogous compound, ETHOQUAD 18/25, was one of the most effective surfactants tested.

Despite the extensive studies and efforts devoted to improving the performance of glyphosate, a need exists for a way of potentiating the effectiveness of glyphosate salts such as the amine, sodium, alkylsulfonium, alkylphosphonium, sulfonylamine, and aminoguanidine salts thereof by means of an environmentally friendly aqueous formulation made from a small number of ingredients, wherein the amounts of each of the components, including the glyphosate, can be kept very small, and wherein the resulting composition provides clearly observable herbicidal or plant regulant action. It would be particularly desirable if this need could be fulfilled by use of readily available, cost-effective materials while at the same time avoiding the inclusion of polyvalent metal-containing and metalloid-containing components in the formulation.

This invention is deemed to fulfill the foregoing need in an effective and highly efficient manner.

THE INVENTION

This invention involves the discovery, inter alia, that certain double-tailed alkanol polyethoxylates are effective as adjuvants for increasing the phytotoxic and plant growth regulant effectiveness of glyphosate against a certain plant species, particularly in control of certain undesirable broadleaf species. Thus this invention makes it possible to achieve enhanced phytotoxic and plant growth regulant effectiveness in an aqueous solution formed from as few as two added ingredients, both of which are readily available in the marketplace. Moreover it is possible pursuant to this invention to employ the glyphosate herbicide in dosage levels substantially lower than currently recommended. Also, within these lower dosage levels it is possible, as will be seen hereinafter, to achieve at least some selective herbicidal or plant growth regulant action as between certain different broadleaf species. Furthermore, the adjuvants used in the practice of this invention are in themselves environmentally friendly. And in addition, the formulation requires no polyvalent metal or metalloid components in its formation. Indeed the preferred compositions are devoid of metal and metalloid additive content, and most preferably contain only the elements C, H, O, N, P, and optionally S. Moreover, the liquid concentrates are most preferably formed using deionized water.

The adjuvants used in forming the formulations of this invention are one or more water-soluble polyethoxylated monohydric alcohols having a β-branched alkyl group having a total of at least about 10 carbon atoms and at least about 3 carbon atoms in the branch on the β-carbon atom (sometimes referred to herein as "double-tailed ethoxylate adjuvants"). By water-soluble is meant that the component is soluble to at least the extent of 1% by weight in deionized water at 25° C. When used in forming an aqueous concentrate of this invention, the adjuvant should have a water solubility of at least 5% by weight in deionized water at 25° C.

In accordance with one of its embodiments this invention provides a method of controlling vegetation by applying to plant foliage, preferably by spraying, a solution (preferably a polyvalent metal-free and metalloid-free solution) containing an effective herbicidal or plant growth regulant mount of a composition formed by intimately mixing the following ingredients with water:

(a) at least one agriculturally acceptable amine, alkali metal, alkylsulfonium, alkylphosphonium, sulfonylamine, and/or aminoguanidine salt of glyphosate; and (b) at least one of the above water-soluble double-tailed ethoxylate adjuvants.

Another embodiment of this invention is a herbicide or plant growth regulant formulation which comprises a solution containing an effective herbicidal or plant growth regulant amount of a composition formed by intimately mixing components (a) and (b) above with water. Optionally, one or more substances, most preferably that are not herbicides, or plant growth regulants, or surfactants, such as dyes, humectants, corrosion inhibitors, stickers, spreaders and thickeners, can be included as component (c) in these formulations.

Still another embodiment of this invention is a powder or granular herbicide or plant growth regulant formulation which comprises a mixture containing an effective herbicidal or plant growth regulant amount of a composition formed by intimately mixing together components (a) and (b), and optionally including one or more of (c) above. Such compositions can also be formed by evaporating to dryness (e.g., by spray drying, extrusion or pan granulation) a solution of components (a) and (b) above, and optionally (c) above. Application of the powder formulations to vegetation as foliar dusts for effecting control of the vegetation constitutes another embodiment of this invention.

It will be appreciated that to effect control of undesired plant vegetation pursuant to this invention, recourse may be had to herbicidal activity whereby undesired vegetation is killed and/or to plant growth regulant activity whereby the further growth of the vegetation is stunted, inhibited and/or slowed without actually killing all of the undesired vegetation treated with the composition.

The herbicidal (phytotoxic) and the plant growth regulant compositions of this invention include aqueous concentrates which can be shipped and stored until diluted with more water on site to produce the final solution for application to the foliage as by spraying. Likewise the herbicidal and the plant growth regulant compositions of this invention include the more dilute aqueous solutions for use in application to the foliage. These more dilute aqueous solutions are preferably formed simply by suitably diluting an aqueous concentrate of this invention with water (if a powder or granular concentrate) or with more water (if a liquid concentrate) to achieve the appropriate herbicidal or plant regulant dosage, but alternatively, can be formed on site by intimately mixing the separate ingredients or sub-combinations thereof with sufficient water on site to achieve the appropriate dosage. Use of the solid or liquid concentrates of this invention is preferable as it is a much simpler operation and minimizes the possibility of blending errors. Moreover, if desired, other components such as fertilizers, penetrants, spreaders, stickers, etc., can be introduced into the final solution at the time the concentrate is blended with water to form the diluted solution for application to the foliage.

Component (a)

The identities and methods for the preparation of the glyphosate ingredient of the formulation are well known and are reported in the literature. See for example, U.S. Pat. No. 3,799,758 to J. E. Franz which describes amine salts and alkali metal salts of glyphosate, and the production of glyphosate by such methods as the phosphonomethylation of glycine, the reaction of ethyl glycinate with formaldehyde and diethylphosphite, and the oxidation of the corresponding aminophosphinic compounds. Another method involves conducting a Mannich reaction with phosphorous acid and formaldehyde on iminodiacetic acid followed by controlled oxidation to N-(phosphonomethyl)glycine. Typically the amine of the glyphosate amine salts has a molecular weight of less than 300. A preferred amine salt of glyphosate is a salt formed with isopropyl amine. Of the alkali metal salts of glyphosate, sodium is the preferred cation. Inasmuch as glyphosate has more than one replaceable hydrogen atom, either or both of mono- and dialkali metal salts of glyphosate can be formed and used. The alkylsulfonium salts of glyphosate are described for example in U.S. Pat. No. 4,315,765 to G. B. Large, and analogous procedures can be used for producing alkylphosphonium salts. Of the alkylsulfonium and alkylphosphonium salts, the trimethylsulfonium salt of glyphosate is preferred. Sulfonylamine and amiguanidine salts of glyphosate which are also suitable for use pursuant to this invention are disclosed in EP-A-0 088 180. The patent literature contains numerous additional references to various other methods for the production of glyphosate. See for example U.S. Pat. Nos. 4,851,159; 4,898,972; 4,937,376; 4,952,723; 5,061,820; and 5,072,033 to Fields Jr. et al., 5,023,369 to Fields, Jr.; 4,853,159 to Riley et. al; and 5,047,579 to Glowka et al., as well as relevant references cited in these patents. Fields, Jr. et al. U.S. Pat. No. 4,965,403 describes a process for producing the alkali metal salts of glyphosate. Aqueous solutions of glyphosate salts devoid of other adjuvants are commercially available from Monsanto Company and these solutions are suitable for use in forming the compositions of this invention.

Component (b)

This component in the form added to the water or aqueous solution is one or more water-soluble polyethoxylated monohydric alcohols having a β-branched alkyl group having a total of at least about 10 carbon atoms and at least about 3 carbon atoms in the branch on the β-carbon atom. Typically, they contain in the range of from about 2 to about 24 ethoxy groups per molecule. If desired, component b) can be a water-soluble agriculturally acceptable derivative of such polyethoxylates, such as an agriculturally acceptable univalent salt such as the lithium, sodium, or potassium salt, or an agriculturally acceptable ester of an inorganic acid (e.g., sulfate, phosphate, nitrate, etc.), or an organic acid (e.g., an acetate, formate, oxalate, etc.,). Preferably the β-branched alkyl group has a total of at least about 12 carbon atoms, and at least about 4 carbon atoms in the branch on the β-carbon atom. More preferably, the β-branched alkyl group has a total of in the range of from about 14 to about 24 carbon atoms, and from about 5 to about 10 carbon atoms in the branch on the β-carbon atom. Still more preferably, the β-branched alkyl group has a total in the range of from about 16 to about 20 carbon atoms, and from about 6 to about 8 carbon atoms in the branch on the β-carbon atom. Most preferably, the alkyl group is bifurcated on the β-carbon atom into a pair of chains or tails, one of which has two more carbon atoms than the other. In all cases the number of ethoxy groups per molecule will be sufficient to render the compound water-soluble. Thus as a general rule, the higher the molecular weight of the alkanol, the higher the number of ethoxy groups in the ethoxylated alkanol.

The double-tailed ethoxylate adjuvants when in ethoxylated alcoholic form can be represented by the following formula:

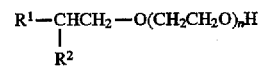

where $R^1$ is an alkyl group (preferably a linear alkyl group) having in the range of about 5 to about 12 or more carbon atoms, $R^2$ is an alkyl group (preferably a linear alkyl group) having in the range of about 3 to about 10 or more carbon atoms (most preferably with $R^1$ having two carbon atoms more than $R^2$), n is an integer in the range of from about 2 to about 24 (which in most cases is an average number within this range). As noted above, this component can be a single compound or a combination or mixture of two or more compounds.

Methods for producing the double-tailed ethoxylate adjuvants are known and are reported in the literature. Typically they involve ethoxylating an alkanol having a branch on the β-carbon atom. See for example U.S. Pat. No. 3,887,624 which describes formation of ethoxylated β-branched alcohols. The β-branched alcohols can be produced by the so-called Guerbet reaction in which a normal primary alcohol is heated with a sodium alkoxide in the presence of a nickel catalyst. Other methods include the well-known oxo process, and the controlled oxidation and hydrolysis of β-branched aluminum alkyls. Suitable compounds of the above formula are available as articles of commerce.

Table 1 sets forth general and preferred proportions for use in forming the liquid concentrate formulations of this invention. The percentages given in Table 1 are weight percentages, and represent weight percent of the total composition. The percentages for the amine, alkali metal, alkylsulfonium, alkylphosphonium, sulfonylamine, and/or aminoguanidine glyphosate salt ("Glyphosate Salt") used in the practice of this invention as given in Table 1 are on an active ingredient basis and are in terms of glyphosate acid equivalent (i.e., the weight of the particular salt-forming portion of the product is excluded from the weight of the salt). Likewise the amount of any water associated with the salt as received is excluded from consideration as regards the percentages of the Glyphosate Salt shown in Table 1.

TABLE 1

| Ingredient | General Range, wt % | Preferred Range, wt % |
| --- | --- | --- |
| Component (a) | 0.1 to 65% | 18 to 65% |
| Component (b) | 1 to 70% | 10 to 25% |
| Other Ingredient(s) | 0 to 20% | 0 to 5% |
| Water | Balance to 100% | Balance to 100% |

Table 2 sets forth the proportions which can be used in forming the powder or granular compositions of this invention. As in Table 1, the percentages given in Table 2 are weight percentages on an active ingredient basis, and represent weight percent of the total composition. And as above, the percentages for the amine, alkali metal, alkylsulfonium, alkylphosphonium, sulfonylamine, and/or aminoguanidine glyphosate salt ("Glyphosate Salt") used in the practice of this invention as given in Table 2 are in terms of glyphosate acid equivalent.

TABLE 2

| Ingredient | General Range, wt % | Preferred Range, wt % |
| --- | --- | --- |
| Component (a) | 10 to 99% | 75 to 98% |
| Component (b) | 1 to 90% | 2 to 25% |
| Other Ingredient(s) | 0 to 20% | 0 to 10% |

The diluted solutions for application to the plant foliage are typically formed prior to application using a tank mixer, spray tank or similar apparatus. The dosage level of the composition applied to the plant foliage will depend to some extent upon the plant species being treated, the extent of control desired, and the prevailing weather conditions. Generally speaking, however, the amount applied will be a herbicidally or plant growth regulant amount falling within the range of about 50 to about 1250 grams of glyphosate (on an acid equivalent basis, i.e., excluding the weight of the cationic salt associated therewith) per hectare. In terms of ounces avoirdupois per acre this range corresponds (on the same acid equivalent basis) to from about 0.7 to about 20 ounces of glyphosate per acre). In accordance with this invention it is preferred to employ a herbicidal or plant growth regulant amount (again on an acid equivalent basis) falling within the range of about 200 to about 830 grams of glyphosate per hectare which corresponds (on the same acid equivalent basis) to about 3 to about 12 ounces avoirdupois of glyphosate per acre), as this is generally sufficient to control most undesired plant species, is below the dosage currently recommended for herbicidal use of glyphosate formulations, and is thus more economical and environmentally friendly. On the basis of this disclosure and the new technology described herein, it is now possible to make departures from the foregoing ranges whenever such is deemed necessary or desirable in any given situation.

In preferred embodiments of this invention the aqueous solutions are composed exclusively of one or more of the glyphosate salts, one or more double-tailed ethoxylate adjuvants of this invention, and water. Likewise the powder or granular mixtures adapted for dilution on site for application in liquid form and also the powder mixtures adapted for application as foliar dusts are composed exclusively of one or more of the glyphosate salts and one or more double-tailed ethoxylate adjuvants of this invention.

The following non-limiting Examples illustrate the practice and advantages of this invention.

EXAMPLES

A field test was conducted in which the effectiveness of compositions of this invention was compared with effectiveness of a standard recommended glyphosate formulation. The test formulations of this invention consisted of the aqueous solution made from (a) N-(phosphonomethyl) glycine isopropyl amine salt, (b) a mixture of polyethoxylated 2-hexyl-1-octanol having an average of about 15 ethoxy groups per molecule, and (c) water. No other component or ingredient was employed in forming these test formulations.

The glyphosate used in forming these formulations was ROUND-UP® D-Pak from Monsanto, which is a 62.0% aqueous solution of the glyphosate isopropyl amine salt in water with no other component therein. The control formulation was an aqueous solution of N-(phosphonomethyl) glycine isopropyl amine salt and the commercial adjuvant INDUCE® (Helena Chemical Company) which, according to *A Guide to Agricultural Spray Adjuvants Used in the United States,* by T. L. Harvey, 1992–93 Edition, Thomson Publications, Fresno, Calif., page 33 is alkyl polyoxyalkane ether, free fatty acids and IPA, which is an adjuvant currently recommended for use in glyphosate formulations. The control formulation was applied at the recommended dosage level of 15 fluid ounces of glyphosate (active ingredient basis) per acre (624 grams of glyphosate per hectare) whereas the formulations of this invention were applied at dosages of only 5 and 10 fluid ounces of glyphosate per acre (209 and 416 grams of glyphosate per hectare, respectively, on an active ingredient basis). All solutions of the invention contained one percent by weight of the double-tailed ethoxylate adjuvant.

All tests were conducted at the same experimental test site at the same time, and were performed with three replicate tests for each composition, using randomized plots. Each plot was 10 feet by 15 feet (ca. 3.1 meters by ca. 4.6 meters) in size. Single applications were made between 10:00 a.m. and 2:30 p.m. on the same calm, sunny day with a relative humidity reading of 75% and an air/soil temperature of 85° F. and 92° F. (ca. 29° C. and ca. 33° C.), respectively. The application was made with a carbon dioxide pressurized back pack sprayer. The soil and leaf conditions were both dry at the time of application.

The population of weed species in the plots included the following:

1 to 4 square feet of barnyard grass and crab grass (3–5 inches in height, with 2 to 4 leaves per plant).

2 to 5 square feet of red weed (3–6 inches in height, with 3 to 6 leaves per plant).

0 to 2 square feet of hemp sesbania (2–5 inches in height, with 3 to 5 leaves per plant).

1 to 3 square feet of morning glory (3–10 inches in height).

3 to 5 square feet of sickle pod (3–7 inches in height, with 3 to 6 leaves per plant).

Observations of percentage of control were made at 7 days and 19 days after application, and Table 3 summarizes the results obtained in these tests. In Table 3 the results are shown in terms of their statistical significance within 95% confidence limits. Thus the symbol ⊕ signifies that the test formulation of this invention gave results that statistically were equivalent to results given by the control. In every case the glyphosate dosage level in the formulations of this invention was only a fraction (33% or 67%) of the glyphosate dosage level in the control formulation. The symbol ⊖ signifies that statistically the result was not equivalent to that of the control but nevertheless demonstrated growth regulant activity. Barnyard grass and crab grass are designated as "BYG and CG" in Table 3.

TABLE 3

Control of Plant Species Under Field Conditions

| Plant Species | Glyphosate Dosage, % of Control Dosage | Result, 7 Days | Result, 19 Days |
| --- | --- | --- | --- |
| BYG and CG | 33% | ⊕ | ⊖ |
| BYG and CG | 67% | ⊖ | ⊖ |
| Red Weed | 33% | ⊕ | ⊖ |
| Red Weed | 67% | ⊕ | ⊖ |
| Hemp Sesbania | 33% | ⊖ | ⊖ |
| Hemp Sesbania | 67% | ⊕ | ⊕ |
| Morning Glory | 33% | ⊖ | ⊕ |
| Morning Glory | 67% | ⊖ | ⊕ |
| Sickle Pod | 33% | ⊖ | ⊕ |
| Sickle Pod | 67% | ⊖ | ⊕ |

Optionally, one or more other substances can be employed in the formulations of this invention provided no such substance materially detracts from the effectiveness of the composition in combatting the particular plant species to be controlled by use of the formulation. By "materially" in this context is meant that in tests conducted by concurrent application under identical conditions and using identical dosages of one or the other of two (2) test formulations to a plant species in three (3) identical pairs of test plots (each pair consisting of a Case I plot and a Case II plot) in the same substantially uniform test site, where in Case I the formulation of this invention does not contain such additional substance(s) whereas in Case II the identical formulation does additionally contain such additional substance(s), there is a reduction in the average percentages of the plant species controlled in the three (3) Case II plots as compared to the average percentages of the plant species controlled in the three (3) Case I plots, and the arithmetic difference between these averages exceeds 10%. Such other substances that may be used if they do not materially detract from the effectiveness of the composition include dyes, pigments, humectants, corrosion inhibitors, thickeners, adhering agents (stickers), spreading agents, other herbicides, and like materials. Such other substances can be introduced into the formulation in any sequence relative to components (a) and (b) hereof, i.e., such materials can be added before, after or at the same time as either or both of components (a) and (b). In this connection, while one or more additional herbicides can be used in the compositions of this invention, most preferably the one or more glyphosate salts constitute(s) the only herbicide(s) or plant growth regulant(s) used in forming the compositions of this invention. Likewise most preferably one or more of the herein-described polyethoxylated monohydric alcohols constitute(s) the only surfactant(s) used in the practice of this invention. This ensures that the substantial benefits provided by this invention are realized in full.

The powder or granular formulations of this invention may be mixed with a finely-divided solid diluent such as talc, gypsum, Fuller's earth, kaolin, kieselguhr, bentonite, dolomite, calcium carbonate, and powdered magnesia. They may also be formulated as dispersible powders or grains, and in this case it is desirable to include a wetting agent to facilitate the dispersion of powder or grains in the liquid carrier. Additionally, formulations in the form of powders can be applied to vegetation as foliar dusts.

It is to be understood that the terms "ingredient" or "component" or "substance" as used anywhere in the specification or claims hereof, whether used in the singular or plural, are used in the sense that it is a substance employed in forming the powder or granular concentrate or aqueous solution, and thus at least prior to mixing with other ingredients or components and/or addition to an aqueous medium, the ingredient or component is in the chemical form specified. It matters not what chemical changes, transformations and/or reactions, if any, take place in file mixture or aqueous medium itself as such changes, transformations and/or reactions are the natural result of bringing the specified ingredients or components together as solids or in an aqueous medium.

Each and every patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A method of controlling vegetation which comprises applying to plant foliage an effective herbicidal or growth regulant amount of a composition formed by intimately mixing the following components with water:

a) at least one agriculturally acceptable amine, alkali metal, alkylsulfonium, alkylphosphonium, sulfonylamine, and/or aminoguanidine salt of glyphosate; and b) at least one water-soluble polyethoxylated monohydric primary alcohol having a β-branched alkyl group which has a total of at least about 10 carbon atoms and at least about 3 carbon atoms in the branch on the β-carbon atom or agriculturally acceptable salt or ester thereof.

2. A method according to claim 1 wherein component a) is an amine or alkylsulfonium salt of glyphosate.

3. A method according to claim 1 wherein component a) is the isopropyl amine salt of glyphosate.

4. A method according to claim 1 wherein component a) is the only herbicide used forming said composition.

5. A method according to claim 1 wherein component b) is at least one ethoxylated alkanol represented by the following formula:

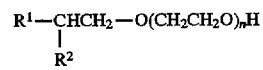

where $R^1$ is an alkyl group having in the range of about 5 to about 12 carbon atoms, $R^2$ is an alkyl group having in the range of about 3 to about 10 carbon atoms, n is an integer in the range of from about 2 to about 24.

6. A method according to claim 5 wherein $R^1$ and $R^2$ are both linear alkyl groups, wherein $R^1$ has two carbon atoms more than $R^2$, and wherein n is an average number within the range of about 2 to about 24.

7. A method according to claim 1 wherein component b) consists essentially of polyethoxylated 2-hexyl-1-octanol having an average of about 15 ethoxy groups per molecule.

8. A method according to claim 1 wherein component a) is an amine salt of glyphosate and wherein component b) is at least one ethoxylated alkanol represented by the following formula:

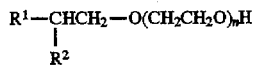

where $R^1$ is an alkyl group having in the range of about 5 to about 12 carbon atoms, $R^2$ is an alkyl group having in the range of about 3 to about 10 carbon atoms, n is an integer in the range of from about 2 to about 24.

9. A method according to claim 8 wherein $R^1$ and $R^2$ are both linear alkyl groups, wherein $R^1$ has two carbon atoms more than $R^2$, and wherein n is an average number within the range of about 2 to about 24.

10. A method according to claim 9 wherein the isopropyl amine salt of glyphosate is the only herbicide used in forming said composition.

11. A method according to claim 1 wherein component a) is an amine salt of glyphosate and wherein component b) consists essentially of polyethoxylated 2-hexyl-1-octanol having an average of about 15 ethoxy groups per molecule.

12. A composition which comprises a solution containing at least a herbicidally or plant growth regulating amount of a composition formed by intimately mixing the following components with water:
   a) at least one agriculturally acceptable amine, alkali metal, alkylsulfonium, alkylphosphonium, sulfonylamine, and/or aminoguanidine salt of glyphosate; and
   b) at least one water-soluble polyethoxylated monohydric primary alcohol having a β-branched alkyl group which has a total of at least about 10 carbon atoms and at least about 3 carbon atoms in the branch on the β-carbon atom or agriculturally acceptable salt or ester thereof.

13. A composition according to claim 12 wherein component a) is an amine or alkylsulfonium salt of glyphosate.

14. A composition according to claim 12 wherein component a) is the isopropyl amine salt of glyphosate.

15. A composition according to claim 12 wherein component a) is the only herbicide used in forming said composition.

16. A composition according to claim 12 wherein component b) is at least one ethoxylated alkanol represented by the following formula:

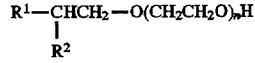

where $R^1$ is an alkyl group having in the range of about 5 to about 12 carbon atoms, $R^2$ is an alkyl group having in the range of about 3 to about 10 carbon atoms, n is an integer in the range of from about 2 to about 24.

17. A composition according to claim 16 wherein $R^1$ and $R^2$ are both linear alkyl groups, wherein $R^1$ has two carbon atoms more than $R^2$, and wherein n is an average number within the range of about 2 to about 24.

18. A composition according to claim 12 wherein component b) consists essentially of polyethoxylated 2-hexyl-1-octanol having an average of about 15 ethoxy groups per molecule.

19. A composition according to claim 12 wherein component a) is an amine salt of glyphosate and wherein component b) is at least one ethoxylated alkanol represented by the following formula:

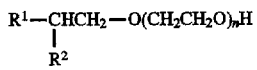

where $R^1$ is an alkyl group having in the range of about 5 to about 12 carbon atoms, $R^2$ is an alkyl group having in the range of about 3 to about 10 carbon atoms, n is an integer in the range of from about 2 to about 24.

20. A composition according to claim 19 wherein $R^1$ and $R^2$ are both linear alkyl groups, wherein $R^1$ has two carbon atoms more than $R^2$, and wherein n is an average number within the range of about 2 to about 24.

21. A composition according to claim 20 wherein the isopropyl amine salt of glyphosate is the only herbicide used in forming said composition.

22. A composition according to claim 12 wherein component a) is an amine salt of glyphosate and wherein component b) consists essentially of polyethoxylated 2-hexyl-1-octanol having an average of about 15 ethoxy groups per molecule.

23. A composition according to claim 12 wherein the solution (i) is devoid of metal and metalloid additive content other than the phosphorus of the glyphosate, (ii) is an aqueous concentrate adapted for dilution with water before use, and (iii) is formed using deionized water.

24. A composition according to claim 12 wherein the solution (i) is devoid of metal and metalloid additive content other than the phosphorus of the glyphosate, (ii) is a dilute aqueous solution adapted for direct application to at least one plant species, and (iii) is devoid of any herbicide other than said component a).

25. A composition which comprises a powder or granular mixture containing at least a herbicidally or plant growth regulating amount of a composition formed by intimately mixing together the following components:
   a) at least one agriculturally acceptable amine, alkali metal, alkylsulfonium, alkylphosphonium, sulfonylamine, and/or aminoguanidine salt of glyphosate; and
   b) at least one water-soluble polyethoxylated monohydric primary alcohol having a β-branched alkyl group which has a total of at least about 10 carbon atoms and at least about 3 carbon atoms in the branch on the β-carbon atom or agriculturally acceptable salt or ester thereof.

26. A composition according to claim 25 wherein component a) is an amine or alkylsulfonium salt of glyphosate.

27. A composition according to claim 25 wherein component b) is at least one ethoxylated alkanol represented by the following formula:

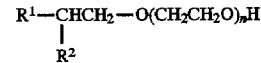

where $R^1$ is an alkyl group having in the range of about 5 to about 12 carbon atoms, $R^2$ is an alkyl group having in the range of about 3 to about 10 carbon atoms, n is an integer in the range of from about 2 to about 24.

28. A composition according to claim 27 wherein $R^1$ and $R^2$ are both linear alkyl groups, wherein $R^1$ has two carbon atoms more than $R^2$, and wherein n is an average number within the range of about 2 to about 24.

29. A composition according to claim 27 wherein component a) is an amine or alkylsulfonium salt of glyphosate, and is the only herbicide used in forming said composition.

30. A composition according to claim 28 wherein component a) is the isopropyl amine salt of glyphosate or the trimethylsulfonium salt of glyphosate, and wherein component b) consists essentially of polyethoxylated 2-hexyl-1-octanol having an average of about 15 ethoxy groups per molecule.

31. A method of controlling vegetation which comprises applying to plant foliage a herbicidal or plant growth regulant amount of a polyvalent metal-free and metalloid-free herbicide or plant growth regulant composition formed by intimately mixing together the following ingredients:

a) at least one agriculturally acceptable amine, alkali metal, alkylsulfonium, alkylphosphonium, sulfonylamine, or aminoguanidine salt of glyphosate as the only herbicide(s) or plant growth regulant(s) used in forming said composition;

b) at least one water-soluble polyethoxylated monohydric primary alcohol having a β-branched alkyl group which has a total of at least about 10 carbon atoms and at least about 3 carbon atoms in the branch on the β-carbon atom or agriculturally acceptable salt or ester thereof, as the only surfactant(s) used in forming said composition; and c) optionally, one or more agriculturally acceptable substances none of which is a herbicide, or a plant growth regulant or a surfactant.

32. A method according to claim 31 wherein said herbicide or plant growth regulant composition is in the form of a water solution, and wherein said composition is applied to the foliage as a spray.

33. A method according to claim 31 wherein said herbicide or plant growth regulant composition is in the form of a powder, and wherein said composition is applied to the foliage as a foliar dust.

* * * * *